US007915033B2

(12) United States Patent
Higashi et al.

(10) Patent No.: US 7,915,033 B2
(45) Date of Patent: Mar. 29, 2011

(54) INCUBATION CONTAINER SYSTEM

(75) Inventors: Len Higashi, Pearl City, HI (US); Fernd Engelen, Bothell, WA (US); Peter Bristol, Shoreline, WA (US); Cathy Owen, Honolulu, HI (US); Dan Blase, Everett, WA (US); Dexter Poon, Honolulu, HI (US)

(73) Assignee: Nanopoint, Inc., Honolulu, HI (US)

(*) Notice: Subject to any disclaimer, the term of this patent is extended or adjusted under 35 U.S.C. 154(b) by 0 days.

(21) Appl. No.: 12/253,144

(22) Filed: Oct. 16, 2008

(65) Prior Publication Data

US 2010/0097695 A1 Apr. 22, 2010

(51) Int. Cl.
*C12M 1/34* (2006.01)
*C12M 3/00* (2006.01)

(52) U.S. Cl. .................... 435/288.3; 206/455; 206/456; 435/287.1; 359/391

(58) Field of Classification Search .... 435/305.1–305.4, 435/288.3, 287.1; 206/455–456; 359/391; 422/102
See application file for complete search history.

(56) References Cited

U.S. PATENT DOCUMENTS

| | | | | |
|---|---|---|---|---|
| 3,960,658 | A | 6/1976 | Avakian et al. | |
| 4,160,700 | A | 7/1979 | Boomus et al. | |
| 4,255,522 | A | 3/1981 | Fusenig et al. | |
| 4,299,921 | A * | 11/1981 | Youssef | 435/305.4 |
| 4,668,633 | A * | 5/1987 | Walton | 435/305.2 |
| 4,675,298 | A | 6/1987 | Brusewitz | |
| 4,743,556 | A | 5/1988 | Ervin | |
| 4,819,804 | A * | 4/1989 | Levy | 206/456 |
| 5,021,351 | A | 6/1991 | Ervin | |
| 5,147,042 | A * | 9/1992 | Levy | 206/456 |
| 5,520,302 | A | 5/1996 | Anderson et al. | |
| 5,549,213 | A * | 8/1996 | Robbins et al. | 220/8 |
| 5,674,456 | A | 10/1997 | Chess et al. | |
| 6,006,911 | A * | 12/1999 | Levy | 206/456 |
| 6,297,904 | B1 * | 10/2001 | Kitagawa et al. | 359/368 |
| 2003/0217945 | A1 | 11/2003 | Kiene et al. | |
| 2004/0171141 | A1 * | 9/2004 | Plank | 435/287.1 |

OTHER PUBLICATIONS

PCT International Search Report and Written Opinion of the International Searching Authority, issued Dec. 2, 2009, application No. PCT/US09/60718.

* cited by examiner

*Primary Examiner* — Walter D Griffin
*Assistant Examiner* — Shanta G Doe
(74) *Attorney, Agent, or Firm* — Convergent Law Group LLP

(57) ABSTRACT

A method and system for providing a container for investigating at least one specimen are described. The method and system include providing a dish. The dish includes a floor, a plurality of sidewalls, and at least one pedestal. The floor has a perimeter. The plurality of sidewalls coupled with the floor proximate to the perimeter. The at least one pedestal resides on a portion of the floor and is pedestal configured to support at least one microscope slide distal from the floor. The at least one microscope slide bears the specimen(s) for investigation.

34 Claims, 4 Drawing Sheets

INCUBATION CONTAINER SYSTEM

BACKGROUND OF THE INVENTION

Containers for incubating living cells and tissues (e.g., Petri dishes) are employed for many types of biological experiments. Certain experiments grow cells or other biological materials on microscope slides, so that the materials can be inspected or analyzed using a microscope. The containers available for incubating living cells or tissues, however, can be inconvenient when used for slide-based experiments.

Slide-based biological experiments can involve placing a standard glass microscope slide bearing a biological specimen in a conventional incubation container (e.g., a Petri dish), with the slide being covered with a fluid or a reagent. The container can then be incubated for a period of time, for example so that the biological specimen on the slide can grow or otherwise change over time. After incubation, a scientist may wish to remove the microscope slide from the container to examine it using a microscope. Removing the slide from the container is difficult, however, because the slide tends to adhere to the bottom of the container. The adhesion can be attributed to the electrostatic interactions between the positive ends of the polar water molecules and the negatively charged oxygen atoms in the materials forming the glass of the container and the microscope slide. It is particularly difficult to remove a microscope slide from the container bottom when fluid is present. Furthermore, when the scientist endeavors to remove the adherent slide from the container bottom, the forces applied to the slide can cause the specimen to be disturbed, so that the accuracy of the microscopic examination is impaired. With excessive force, the microscope slide can break, with the potential for physical injury to the scientist and the potential for interfering with the overall experiment.

There exists a need in the art, therefore, for an incubation container conveniently sized and shaped for scientific studies that can support a microscope slide for slide-based experiments. Desirably, the microscope slide can be easily inserted into and removed from the container without disturbing any specimen that the slide supports.

BRIEF SUMMARY OF THE INVENTION

A method and system for providing a container for investigating at least one specimen are described. The method and system include providing a dish. The dish includes a floor, a plurality of sidewalls, and at least one pedestal. The floor has a perimeter. The plurality of sidewalls coupled with the floor proximate to the perimeter. The at least one pedestal resides on a portion of the floor and is pedestal configured to support at least one microscope slide distal from the floor. The microscope slide(s) bear the specimen(s) for investigation. In one aspect, the method and system also include providing a lid configured to reside on the plurality of sidewalls.

According to the method and system disclosed herein, the container may allow a slide to be more readily removed from the container, particularly when a fluid is desired to be present. Consequently, investigation of specimens may be facilitated.

DETAILED DESCRIPTION OF THE INVENTION

Figure 1B:
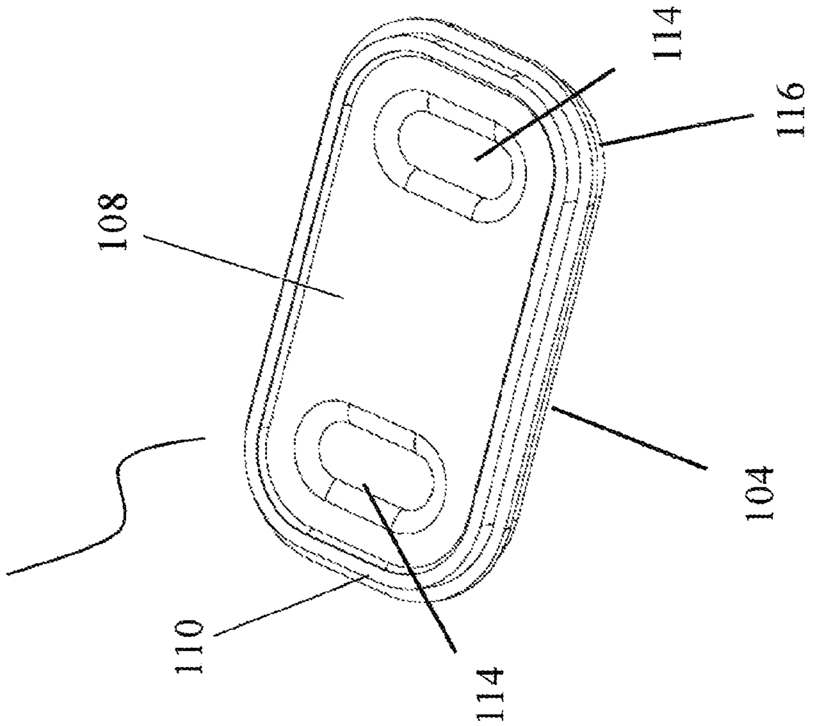
FIG. 1B illustrates the underside of an exemplary embodiment of an incubation dish.

The method and system relate to containers for biological or other material. The following description is presented to enable one of ordinary skill in the art to make and use the invention and is provided in the context of a patent application and its requirements. Various modifications to the embodiments and the generic principles and features described herein will be readily apparent to those of ordinary skill in the art. Thus, the method and system are not intended to be limited to the embodiments shown, but is to be accorded the widest scope consistent with the principles and features described herein. Thus, the method and system are mainly described in terms of particular systems provided in particular implementations. However, one of ordinary skill in the art will readily recognize that this method and system will operate effectively in other implementations. For example, the systems may have differing lengths, aspect ratios, sizes, or take a number of different forms, and/or be used in methodologies and experiments not inconsistent with the method and system.

Disclosed herein is a container for incubating biological materials that may be adapted for supporting a microscope slide and permitting the convenient placement of the slide into the container and the convenient removal of the slide from the container. Thus, the container may be used for investigating one or more specimens. The container may include a container dish and a corresponding lid. In embodiments, the incubation container may include an incubation container dish into which fluid or biological materials can be placed. A lid is configured to cover the dish, restricting evaporation of the fluids from the dish and/or preventing materials from the environment to gain access to the dish contents. In embodiments, the lid may form an airtight seal with the dish. In embodiments, the lid may form a seal with the dish that permits some air exchange or other gas flow.

Projecting superiorly from the base of the container dish are one or more pedestals to support at least one microscope slide. In embodiments, a single pedestal may be situated centrally in the container dish, dimensioned so that the slide balances on it. In another embodiment, the single pedestal may be configured to support the slide near the perimeter of at least part of the slide while leaving the central portion of the slide open, for example for viewing. In other embodiments, a plurality of pedestals may be situated on the base of the container dish, sized and spaced so that they support a microscope slide in a stable manner. In an embodiment, assuming that a conventional microscope slide is about three inches long and one inch wide, a pair of pedestals can be positioned, set apart from about 1.25 to 7 cm. In embodiments, the pedestals can each have a contact area of about 1 $cm^2$, although other dimensions can be chosen so that a microscope slide fits comfortably but is not too loose. In other embodiments, even numbers of pedestals can be positioned to provide stable support for a slide. For example, four, six, or eight appropriately-sized pedestals can be positioned to support the slide. Odd numbers of pedestals can also be used to provide support for the slide.

In embodiments, the pedestals are arranged so that an inverted microscope may have an unimpeded view of the central portion of the slide. For example, the bottom of the container dish may be configured so that it provides across its entirety a viewing area, for example a viewing area of about 27 $cm^2$. If a 3×1 inch slide is to be viewed, then a viewing area of at least about 12.5 $cm^2$ may be used so that the slide can be accessed by an inverted microscope if a pair of pedestals are positioned, for example, about 5 cm apart. Pedestals may be shaped as squares, rectangles, circles, ovals, pyramids or any other shape that can support the microscope slide in a stable manner. When a plurality of pedestals is employed, the pedestals can be positioned in any pattern that allows support of the slide along with microscopic access thereto. In embodiments, the pedestals are positioned so that a technician can readily manipulate the microscope slide digitally or with an instrument.

The pedestals may be formed integrally with the incubation container dish, or the pedestals may be attached to the incubation container dish. If the pedestals are formed integrally with the incubation container, they may be formed from plastic materials by injection molding or milling, and the like. In embodiments, the pedestals may be made of plastic, glass, rubber, metal or ceramic, and affixed to the floor of the dish. In some embodiments, plastic, glass and rubber would be used for biological applications. If the pedestals are attached to the incubation container, they may be attached using glues or epoxies, or the like. Other methods of forming incubation containers with pedestals may also be used.

The pedestals may be dimensioned to support the microscope slide sufficiently close to the bottom of the incubation container dish that an inverted microscope can be used to examine a specimen placed upon the slide. In embodiments, the pedestals are about 4 mm in height, measured from the lowest point on the bottom of the dish to the top surface that would support the slide. Other heights for the pedestals can be designed to account for differences in the type of microscope used, for example, the focal length of the objective lens. For example, taller pedestals may be suitable for applications where lower magnifications and/or longer working distances would be used. In one embodiment, the pedestal height of about 4 mm is selected to permit the ready observation of cells through the bottom of the dish using the 10×objective of an inverted microscope, while also permitting ready manipulation of the slide by a scientist.

In embodiments, the container dish and lid may be made from a variety of materials, depending on the circumstances of its use. For containers where an inverted microscope will be used to inspect the microscope slide that the container bears, the container dish is desirably made from an optically clear material, for example, an optically clear polycarbonate. The dish can be made of a homogeneous material, or it can have specific areas with particular properties. For example, a container dish can embed a lens or a filter in its substance, to permit particular microscopic techniques. In other embodiments, the container dish can be made of other materials, for example, glasses, metals, resins, plastics, ceramics, clay, and the like. In some embodiments, the container dish and lid may be made of different materials, while in other embodiments, the container dish and lid may be made of the same material(s).

For certain biological applications, it is desirable to use a material for the container dish that can withstand exposure to a number of reagents, that has a low degassing value, and that is optically clear. While certain container dishes can, in embodiments, be designed to be disposable after a single use, in other embodiments, it is advantageous to fabricate a container dish that can be used multiple times. Polycarbonate is particularly suitable for biological applications, because it can withstand the conditions in an autoclave, as would be used for sterilizing biological instruments.

Figure 1A:
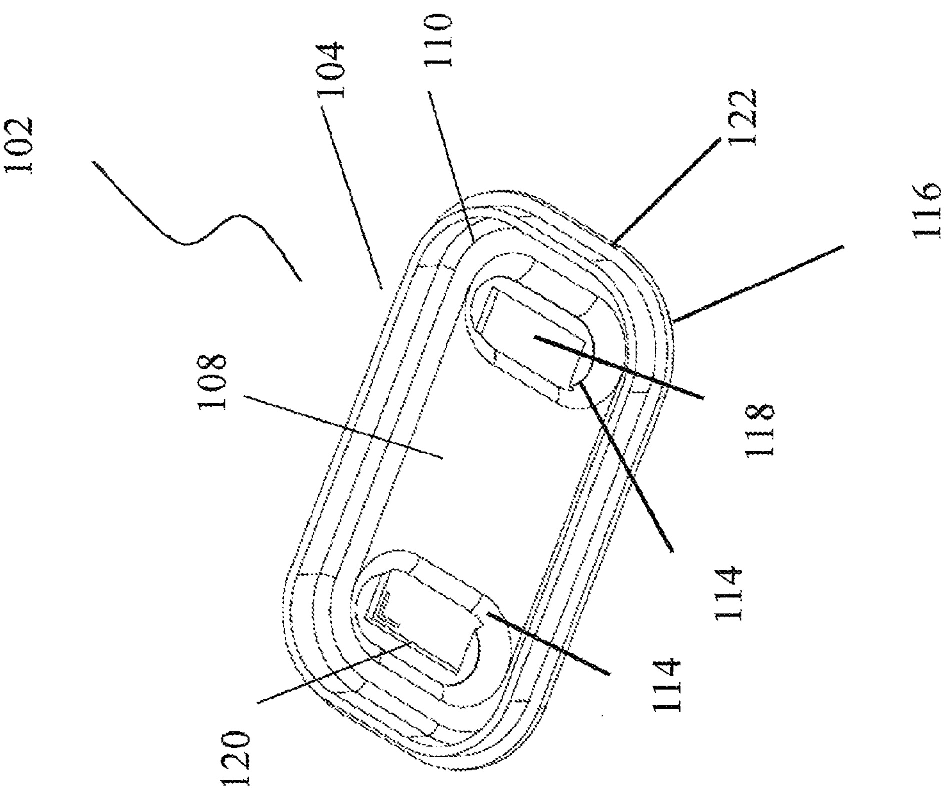
FIG. 1A illustrates the topside of an exemplary embodiment of an incubation dish.

FIG. 1A shows a top, perspective view of an exemplary embodiment of an incubation container dish 102 having a sidewall 104 joining a floor 108. In the depicted embodiment, the sidewall 104 joins the floor 108 through a series of beveled edges 110 that smooth the juncture of sidewall 104 to floor 108. In other embodiments, the sidewall 104 forming a vertical boundary for the incubation dish 102 can join the floor 108 at any angle or as a rounded juncture. Other optional features of the floor 108 can be envisioned, such as a moat (not shown) to hold fluid in a trough surrounding the periphery of the floor 108, or a system of one or more pools (not shown) that contain fluids or reagents situated at specific locations on the floor 108, and formed as depressions in the floor 108. For floors 108 having such optional features, the height of the floor 108 can be elevated so that the moat (not shown) or the pools (not shown) do not project below the bottom of the overall incubation dish 102. The floor 108 is desirably made from an optically clear material so that a microscope imaging system placed under the dish 102 can image a microscope slide (not shown) that is supported by the plurality of pedestals 114 that are formed within the dish 102. In the embodiment shown, the pedestals 114 are configured to support one microscope slide. However, in another embodiment, the pedestals 114 may be configured to support multiple slides. In addition, in some embodiments, the pedestals 114 are configured to support the microscope slide(s) at a distance from the floor 108 that is less than the height of the sidewalls 104. Thus, the microscope slide(s) may be retained between the floor 108 and a lid (not shown in FIG. 1A). The depicted embodiment shows the sidewalls 104 of the incubation dish 102 joining to form rounded corners 116, but in other embodiments, the corners 116 can meet at right angles, or can be formed from several angled panels, or in any other suitable shape. The incubation dish 102 may be sized and shaped to conform to the user's requirements. In an embodiment, it can measure about 4.6 inches in length and 2.6 inches in width, with sidewalls 104 measuring about 0.5 inches in height FIG. 1A shows, in more detail, a plurality of pedestals 114 projecting from the floor 108. In the depicted embodiment, the floor 108 and the sidewall 104 form boundaries in which fluid can be retained. The pedestals each have surfaces 118 that can support a microscope slide (not shown). In one embodiment, the surfaced 118 may be flat. In another embodiment, the surfaces 118 may have another topology capable of supporting a microscope slide. The depicted embodiment of an incubation dish 102 shows a set of ridges 120 on the flat surfaces 118 of the pedestals 114 that can hold the microscope slide in place. The height of the pedestals 114 relative to the floor 108 is such that a technician can conveniently position the microscope slide on the pedestals 114 or remove it therefrom. For example, the pedestals 114 can project about 0.16 inches from the floor 108; other projection amounts can be designed to meet individual user needs. Ridges 120 can be sized proportionately to the dimensions of the pedestals 114 and the incubation dish 102 so that the dish 102 can be covered by a lid (not shown) without the lid impinging upon the ridges 120. In the depicted embodiment, the height of the sidewall 104 exceeds the height of the pedestals 114 so that the microscope slide supported on the pedestals 114 can be immersed in a fluid if desired. On the external aspect of the incubation dish 102 is an outside rim 122 upon which a cover (not shown) for the incubation dish can rest.

FIG. 1B shows an exemplary embodiment of an incubation dish 102 shown from the underside. Rising from the floor 108 are two pedestals 114. In another embodiment, the pedestals 114 may not change the topology of the underside. In the depicted embodiment, the pedestals 114 are formed in continuity with the rest of the dish 102. In other embodiments, the pedestals 114 may be attached as separate structures to the floor 108 of the dish 102. The floor 108 is desirably formed from an optically clear material to permit imaging through it. In the depicted embodiment, the sidewall 104 joins the floor 108 through a series of beveled edges 110 that smooth the juncture of sidewall 104 to floor 108.

Figure 2:
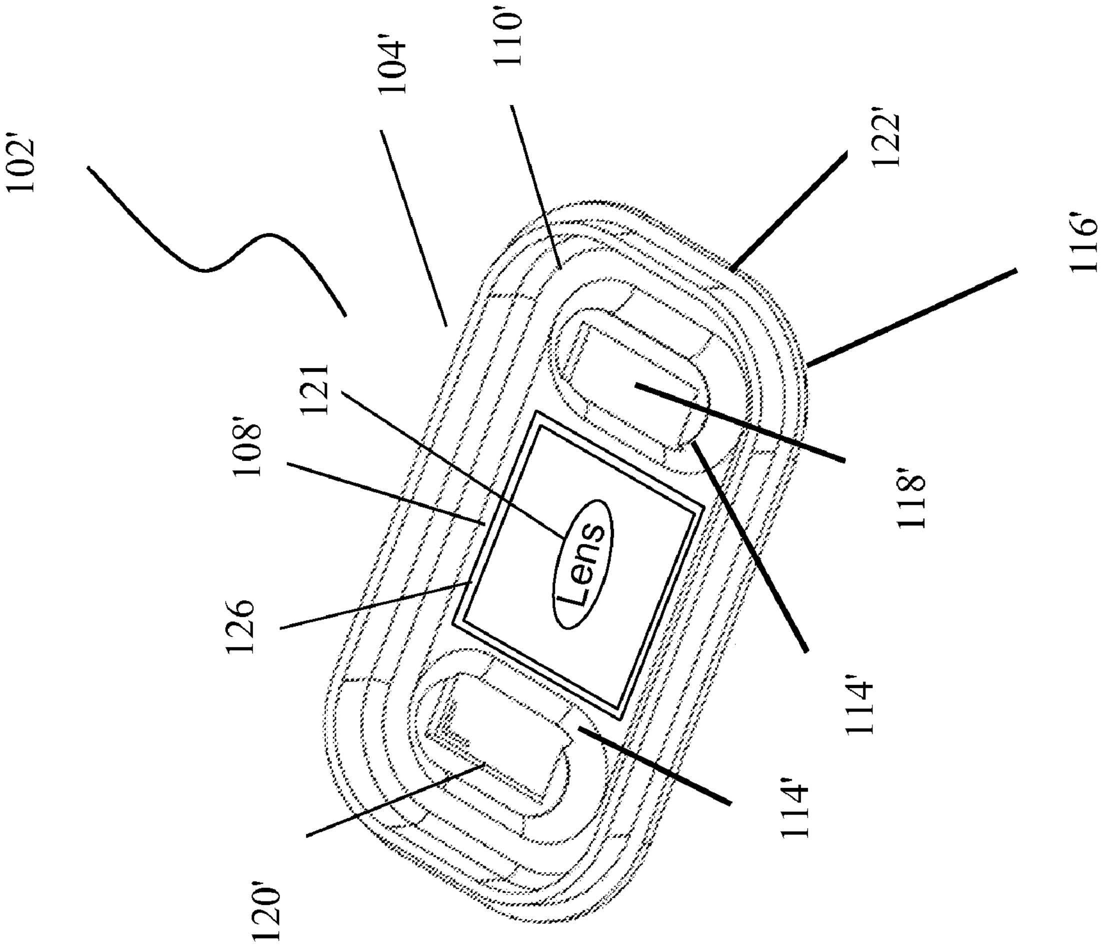
FIG. 2 is a top, perspective view of another exemplary embodiment of an incubation dish

FIG. 2 shows a top, perspective view of another exemplary embodiment of an incubation container dish 102'. The container dish 102' is analogous to the container dish 102. Consequently, analogous components have similar labels. Thus, the container 102' includes sidewalls 104', floor 108', beveled edges 110', pedestals 114', corners 116', surfaces 118', ridges 120', and rim 122', In addition, the container dish 102' includes moat 126 which may be used to hold fluid. The moat 126 is depicted as residing at the periphery of the floor 108' but between the pedestals 114'. However, in another embodiment, the moat 126 may extend at the periphery of the floor 108', having the pedestals 114' interior to the moat 126. In addition, although a single moat 126 is depicted, the container dish 102 may include multiple moats. Further, the moat 126 is depicted as being formed within the floor 108'. However, in another embodiment, the moat 126 may be formed by raised walls. In such an embodiment, a portion of the floor 108' may serve as the bottom of the moat 126.

Figure 3:
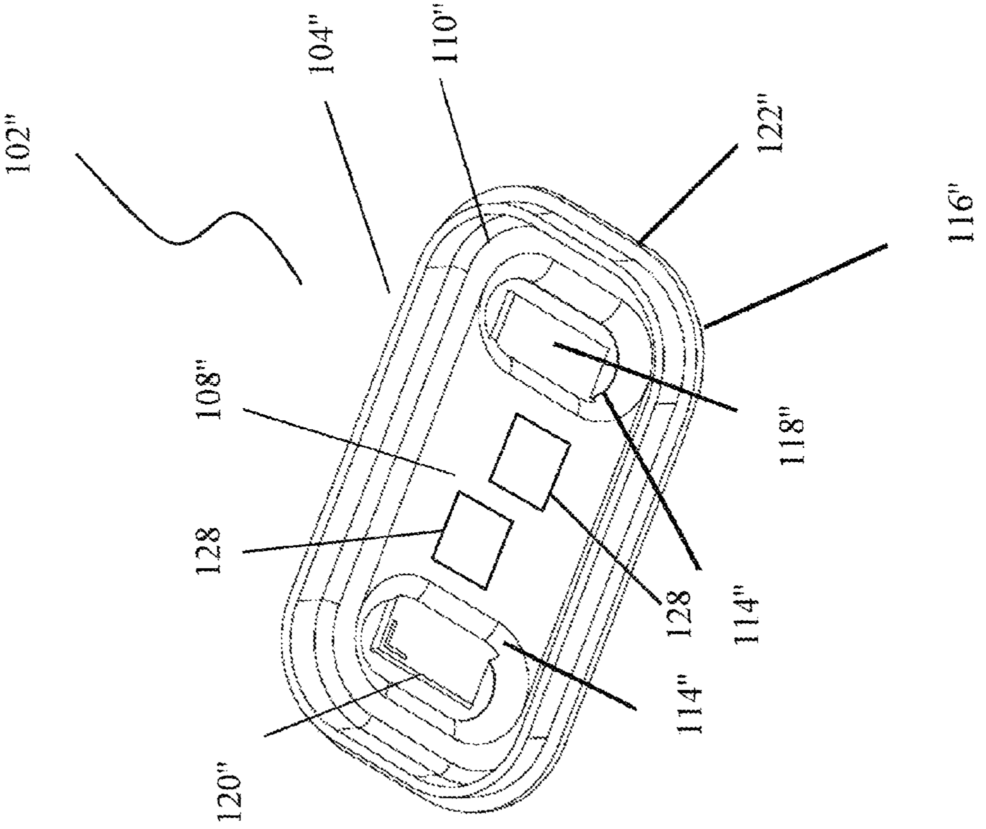
FIG. 3 is a top, perspective view of another exemplary embodiment of an incubation dish

FIG. 3 shows a top, perspective view of another exemplary embodiment of an incubation container dish 102". The container dish 102" is analogous to the container dish 102. Consequently, analogous components have similar labels. Thus, the container 102" includes sidewalls 104", floor 108", beveled edges 110", pedestals 114", corners 116", surfaces 118", ridges 120", and rim 122", In addition, the container dish 102" includes pools 128 which may be used to hold fluid. The pools 128 are depicted as residing between the pedestals 114". However, in another embodiment, the pools 128 may extend to and/or reside at the periphery of the floor 108", closer to the sidewalls 104" than the pedestals 114". Further, the pools 128 are depicted as being formed within the floor 108". However, in another embodiment, the pools 128 may be formed by raised walls. In such an embodiment, a portion of the floor 108" may serve as the bottoms of the pools 128.

Figure 4B:
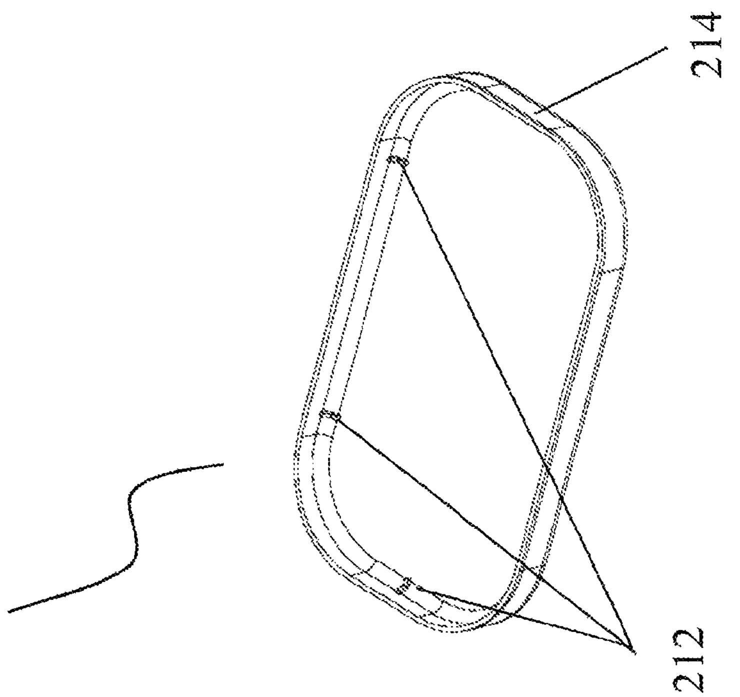
FIG. 4B illustrates the underside of an exemplary embodiment of a lid adapted to cover an incubation dish.
Figure 4A:
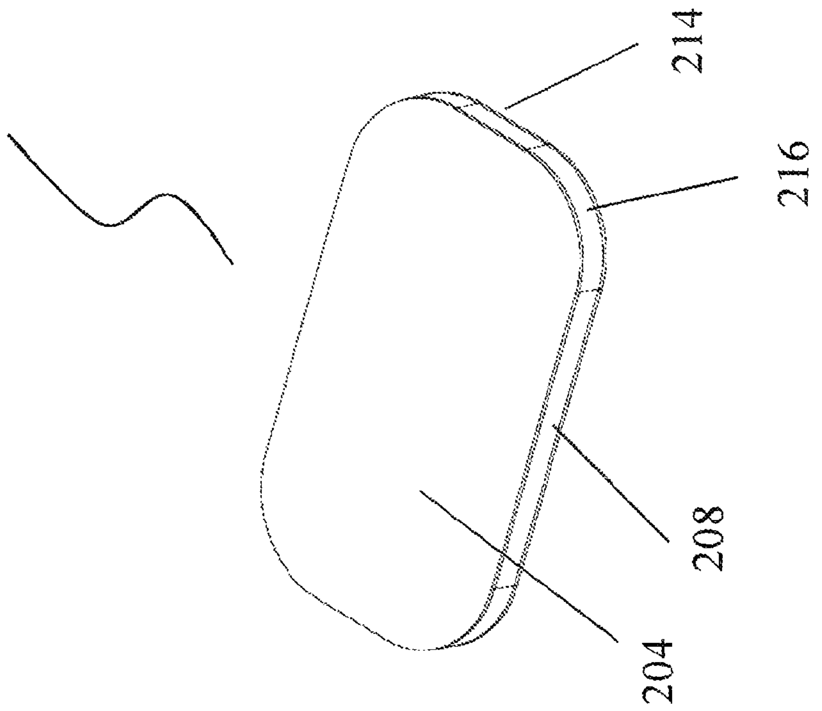
FIG. 4A illustrates the topside of an exemplary embodiment of a lid adapted to cover an incubation dish.

FIG. 4A shows a top view of an embodiment of a lid 202 adapted for use with an incubation dish such as can be seen in FIGS. 1A, 1B, 2, and 3. In the depicted embodiment, the lid 202 has a flat, optically clear top surface 204. In other embodiments, a non-flat surface can be used for the lid 202, and the lid 202 can be used with materials having other optical properties such as a degree of opacity to prevent light from entering the underlying incubation dish, or optically frosted to cut down light exposure. In the depicted embodiment, the lid wall 208 is optically clear as well, although it may be envisioned that the lid wall 208 may be made from materials having other optical properties. Extending vertically downward from the horizontal top surface is a circumferentially disposed lid rim 214, configured to overlap with the sidewalls of an underlying incubation dish (not shown). In an embodiment, the lid 202 can measure about 4.6 inches in length and 2.6 inches in width, corresponding to the dimensions of an underlying incubation dish (not shown), with a lid wall 208 measuring about 0.26 inches in height. The lid rim 214 may bear indentations, projections, or other texturing features (not shown) that facilitate its manipulation. In the depicted embodiment, the corners 210 of the lid are curved, conforming to the shape of the incubation dish as depicted in FIGS. 1A, 1B, 2, and 3. It is understood that the corners 216 desirably conform in shape to the corners of the underlying incubation dish. As shown in FIG. 4B, a plurality of notches 212 may be disposed along the inner aspect of the lid rim 214 to elevate the lid 202 off the underlying incubation dish, thereby allowing an air gap for gas exchange. Without the notches 212, the lid 202 can rest on the top of the incubation dish, providing a relatively gas-tight seal. Optionally, a gasket (not shown) can be provided to produce a more complete gas-tight seal. In another embodiment, the rim 214 may snugly fit the sidewalls of an incubation dish, such as the incubation dish 102. In such an embodiment, once closed the combination of the lid 202 and container dish 102 may retain fluid and/or gas therein.

While the container has been described in connection with certain embodiments, other embodiments would be understood by one of ordinary skill in the art and are encompassed herein. It will be understood that various changes and modifications can be made all within the full and intended scope of the following claims. Accordingly, many modifications may be made by one of ordinary skill in the art without departing from the spirit and scope of the appended claims.

We claim:

1. A container for investigating at least one specimen comprising:

a dish including a floor having a perimeter;

a plurality of sidewalls coupled with the floor proximate to the perimeter; and at least one pedestal residing on a portion of the floor, the at least one pedestal configured to support at least one microscope slide distal from the floor and including a recess therein, the recess configured to retain the at least one microscope slide substantially in place with respect to directions parallel to the floor, the at least one microscope slide bearing the at least one specimen for investigation, the plurality of sidewalls being configured to be capable of retaining a fluid surrounding at least one base of the at least one pedestal.

2. The container of claim 1 wherein the dish further includes at least one moat.

3. The container of claim 2 wherein the floor includes the at least one moat therein, the at least one moat being separated from the plurality of sidewalls by a portion of the floor.

4. The container of claim 2 wherein the dish further includes a plurality of walls residing on the floor, the plurality of walls forming the at least one moat therebetween.

5. The container of claim 1 wherein the dish further includes at least one pool.

6. The container of claim 5 wherein the floor includes the at least one pool therein, the at least one pool being separated from the plurality of sidewalls by a portion of the floor.

7. The container of claim 5 wherein the dish further includes a plurality of walls residing on the floor, the plurality of walls forming the at least one pool therebetween, the at least one pool being separated from the plurality of sidewalls by a portion of the floor.

8. The container of claim 1 wherein the at least one pedestal further includes at least one top surface configured to retain the at least one microscope slide.

9. The container of claim 8 wherein the at least one slide includes a plurality of edges and wherein the at least one surface includes a plurality of ridges configured to retain the at least one slide along at least a portion of the plurality of edges.

10. The container of claim 1 wherein the at least one pedestal further includes a plurality of pedestals.

11. The container of claim 1 wherein the dish further includes a plurality of beveled edges proximate to the perimeter of the floor and to the plurality of sidewalls.

12. The container of claim 1 further comprising:

a lid corresponding to the dish and configured to reside on the plurality of sidewalls.

13. The container of claim 11 wherein the lid includes a rim configured to overlap the plurality of sidewalls.

14. The container of claim 12 wherein the lid includes a gasket for sealing the lid with the plurality of sidewalls.

15. The container of claim 12 wherein the dish includes a gasket for sealing the lid with the plurality of sidewalls.

16. The container of claim 12 wherein at least a portion of the lid is optically transparent.

17. The container of claim 12 wherein the lid includes at least one notch therein, the at least one notch configured to provide at least one gap between the lid and the plurality of sidewalls.

18. The container of claim 1 wherein the plurality of sidewalls extend a first height from the floor and the at least one pedestal extends a second height from the floor, the second height being less than the first height.

19. The container of claim 1 wherein at least a portion of the floor is optically transparent.

20. The container of claim 1 wherein the floor further includes a lens therein.

21. The container of claim 1 wherein the at least one pedestal is configured such that a portion of the at least one microscope slide is viewable from the floor.

22. A container comprising:

a dish including a floor having a perimeter, a plurality of sidewalls coupled with the floor proximate to the perimeter and configured to retain a fluid within the dish and surrounding at least one base of the at least one pedestal; and at least one pedestal residing on a portion of the floor, the at least one pedestal configured to support at least one microscope slide distal from the floor and such that a portion of the at least one microscope slide is viewable from the floor, at least one pedestal including a recess therein, the recess having a topology configured to retain the at least one microscope slide substantially in place with respect to directions parallel to the floor, the at least one microscope slide bearing the at least one specimen for investigation, the floor including at least one of at least one moat and at least one pool therein; and a lid configured to reside on the plurality of sidewalls and be supported thereby, the lid including at least one notch therein, the at least one notch configured to provide at least one gap between the lid and the plurality of sidewalls.

23. A method for providing a container for investigating at least one specimen comprising:

providing a dish including providing a floor having a perimeter;

providing a plurality of sidewalls coupled with the floor proximate to the perimeter; and providing at least one pedestal residing on a portion of the floor, the at least one pedestal configured to support at least one microscope slide distal from the floor and having a recess therein, the recess having a topology configured to retain the at least one microscope slide substantially in place with respect to directions parallel to the floor, the at least one microscope slide bearing at least one specimen for investigation, the plurality of sidewalls being configured to retain a fluid surrounding at least one base of the at least one pedestal.

24. The method of claim 23 further comprising:

providing a lid corresponding to the dish and configured to reside on the plurality of sidewalls.

25. The method of claim 23 wherein the at least one pedestal further includes:

configuring the at least one pedestal such that a portion of the at least one microscope slide is viewable from the floor.

26. A container for investigating at least one specimen comprising:

a dish including means for retaining a fluid; and means for supporting at least one microscope slide distal from the means for retaining the fluid and for retaining the at least one microscope slide substantially in a place, the supporting means including a recess configured to retain the at least one microscope slide substantially in place with respect to directions parallel to a surface of the at least one microscope slide, the at least one microscope slide bearing the at least one specimen for investigation, the fluid retaining means being configured to retain the fluid surrounding the supporting means.

27. The container of claim 1 wherein the at least one pedestal is separated from the plurality of sidewalls by a portion of the floor.

28. The container of claim 1 wherein the plurality of sidewalls forms an outer wall of the dish.

29. The container of claim 22 wherein the at least one pedestal is separated from the plurality of sidewalls by a portion of the floor.

30. The container of claim 22 wherein the plurality of sidewalls forms an outer wall of the dish.

31. The method of claim 23 wherein the at least one pedestal is separated from the plurality of sidewalls by a portion of the floor.

32. The method of claim 23 wherein the plurality of sidewalls form an outer wall of the dish.

33. The container of claim 26 further comprising:

a floor, the fluid retaining means being separated from the supporting means by a portion of the floor.

34. The container of claim 26 wherein the fluid retaining means forms an outer wall of the dish.

* * * * *